United States Patent
Gimi et al.

(10) Patent No.: US 7,115,769 B2
(45) Date of Patent: Oct. 3, 2006

(54) SYNTHESIS OF 2-ALKYLCYSTEINE VIA PHASE TRANSFER CATALYSIS

(75) Inventors: Rayomand H. Gimi, Chelmsford, MA (US); Mukund S. Chorghade, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 332 days.

(21) Appl. No.: 10/438,757

(22) Filed: May 15, 2003

(65) Prior Publication Data

US 2003/0236404 A1    Dec. 25, 2003

Related U.S. Application Data

(60) Provisional application No. 60/392,833, filed on Jun. 27, 2002, provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002.

(51) Int. Cl.
*C07C 323/52* (2006.01)

(52) U.S. Cl. .................. 560/153; 562/557; 552/104
(58) Field of Classification Search ............ 552/104; 562/557; 560/153
See application file for complete search history.

(56) References Cited

U.S. PATENT DOCUMENTS

| | | | |
|---|---|---|---|
| 4,406,905 | A | 9/1983 | Zähner et al. |
| 5,554,753 | A | 9/1996 | O'Donnell et al. |
| 5,840,739 | A | 11/1998 | Bergeron, Jr. |
| 5,872,259 | A | 2/1999 | Reuter |
| 5,929,232 | A | 7/1999 | Jacobsen et al. |
| 6,083,966 | A | 7/2000 | Bergeron, Jr. |
| 6,159,983 | A | 12/2000 | Bergeron, Jr. |
| 6,383,233 | B1 | 5/2002 | Reuter |
| 6,428,583 | B1 | 8/2002 | Reuter |
| 6,521,652 | B1 | 2/2003 | Bergeron |
| 6,525,080 | B1 | 2/2003 | Bergeron |
| 6,559,315 | B1 | 5/2003 | Bergeron |
| 2003/0088105 | A1 | 5/2003 | Krich et al. |
| 2003/0220504 | A1 | 11/2003 | Chorghade et al. |
| 2003/0225287 | A1 | 12/2003 | Chorghade et al. |
| 2003/0229231 | A1 | 12/2003 | Chorghade et al. |
| 2003/0236426 | A1 | 12/2003 | Chorghade et al. |
| 2003/0236434 | A1 | 12/2003 | Gimi et al. |
| 2003/0236435 | A1 | 12/2003 | Gimi et al. |
| 2004/0002613 | A1 | 1/2004 | Chorghade et al. |
| 2004/0006224 | A1 | 1/2004 | Chorghade et al. |
| 2004/0024224 | A1 | 2/2004 | Chorghade et al. |

FOREIGN PATENT DOCUMENTS

| | | |
|---|---|---|
| DE | 20 20 866 A | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |

OTHER PUBLICATIONS

Ehrler, Juerg, and Farooq, Saleem, "Total Synthesis of Thiangazole," *Synlett*, 702-704 (1994).

Kishore, V., et al., "Synthesis of α-Poly-[$N^\epsilon$-(2-aryl-$\Delta^2$-thiazoline-4-carbonyl)-$_L$-lysines] With Antiviral Activity," *Indian Journal of Chemistry 5B*: 255-257 (1977).

Zamri, Adel, and Abdallah, Mohamed A., "An Improved Stereocontrolled Synthesis of Pyochelin, Siderophore of *Pseudomonas aeruginosa* and *Burkholderia cepacia*," *Tetrahedron 56*: 249-256 (2000).

Bergeron, R., et al., "Desazadesmethyldesferrithiocin Analogues as Orally Effictive Iron Chelators," *J. Med. Chem.*, 42:95-108 (1999).

Bergeron, R. et al., "The Desferrithiocin Pharmacophore," *J. Med. Chem.*, 37:1411-1417 (1994).

Bergeron, R. et al., "Effects of C-4 Stereochemistry and C-4 Hydroxylation on the Iron Clearing Efficiency and Toxicity of Desferrithiocin Analogues," *J. Med. Chem.*, 42:2432-2440 (1999).

(Continued)

*Primary Examiner*—Laura L. Stockton
(74) *Attorney, Agent, or Firm*—Hamilton, Brook, Smith & Reynolds, P.C.

(57) ABSTRACT

Non-natural amino acids such as 2-alkylated amino acids allow for the synthesis of a wider variety of peptidal and non-peptidal pharmaceutically active agents. In one embodiment, the present invention provides methods of preparing 2-alkylcysteine derivatives. In another embodiment, the method comprises forming a 2-alkylcysteine derivative from a cysteine derivative in the presence of a phase transfer catalyst. In particular, the present invention provides methods for preparing 2-methylcysteine derivatives.

The present invention also discloses a method of preparing a class of iron chelating agents related to desferrithiocin, all of which contain a thiazoline ring. In one aspect, an aryl nitrile or imidate is condensed with cysteine or a 2-alkyl cysteine. The present invention also relates to the preparation of 4,5-dihydro-2-(2,4-dihydroxyphenyl)-4-alkyl-thiazole-4-carboxylic acids, such as 4,5-dihydro-2-(2,4-dihydroxyphenyl)-4-methyl-thiazole-4-carboxylic acid.

18 Claims, No Drawings

OTHER PUBLICATIONS

Bergeron, R. et al., "Synthesis and Biological Evaluation of Naphthyldesferrithiocin Iron Chelators," *J. Med. Chem.*, 39:1575-1581 (1996).

Bergeron, R. et al., "Evaluation of Desferrithiocin and Its Synthetic Analogues as Orally Effective Iron Chelators," *J. Med. Chem.*, 34:2072-2078 (1991).

Bergeron, R. et al., "Evaluation of the Desferrithiocin Pharmacophore as a Vector for Hydroxamates," *J. Med. Chem.*, 42:2881-2886 (1999).

Bergeron, R. et al., "An Investigation of Desferrithiocin Metabolism," *J. Med. Chem.*, 37:2889-2895 (1994).

Bergeron, R. et al., "A Comparative Study of the Iron-Clearing Properties of Desferrithiocin Analogues with Desferrioxamine B in a *Cebus* Monkey Model," *Blood*, 81(8):2166-2173 (1993).

Bergeron, R. et al., "Pharmacokinetics of Orally Administered Desferrithiocin Analogs in *Cebus Apella* Primates," *Drug Metabolism and Disposition*, 27(12):1496-1498 (1999).

Corey, E. J., et al., "A Rational Approach to Catalytic Enantioselective Enolate Alkylation Using a Structurally Rigidified and Defined Chiral Quaternary Ammonium Salt Under Phase Transfer Conditions," *J. Am. Chem. Soc.*, 119:12414-12415 (1997).

Mulqueen, G. C., et al., "Synthesis of the Thiazoline-based Siderophore (S)-Desferrithiocin," *Tetrahedron*, 49(24):5359-5364 (1993).

O'Donnell, M. J., et al., "α-Methyl Amino Acids by Catalytic Phase-Transfer Aklylations," *Tetrahedron Letters*, 23(41):4259-4262 (1982).

SYNTHESIS OF 2-ALKYLCYSTEINE VIA PHASE TRANSFER CATALYSIS

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, peptidomimetic pharmaceutically active agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)- and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active and/or less toxic forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

In one aspect, the present invention relates to a method of preparing a 2-alkylcysteine derivative represented by Structural Formula (I):

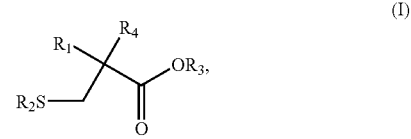

or a salt thereof, wherein $R_1$ is $-NH_2$; $-N(R_5)(R_6)$; $-NHR_7$; or $-N=R_8$; wherein $R_5$, $R_6$, $R_7$, and $R_8$ are, independently, a substituted or unsubstituted alkyl group, a substituted or unsubstituted aromatic group, or a substituted or unsubstituted heterocyclic group;

$R_2$ and $R_3$ are, independently, $-H$, a substituted or unsubstituted alkyl group, a substituted or unsubstituted aromatic group, or a substituted or unsubstituted heterocyclic group; and $R_4$ is a substituted or unsubstituted alkyl group.

In one embodiment, the method comprises reacting a cysteine derivative represented by Structural Formula (II):

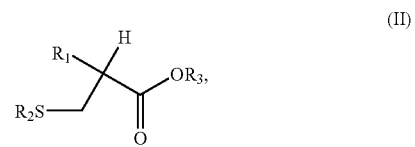

or a salt thereof, wherein $R_1$, $R_2$ and $R_3$ are defined as above, with a compound having the formula $R_4$-L, wherein $R_4$ is defined as above and L is a leaving group, in the presence of a phase transfer catalyst thereby forming the 2-alkylcysteine derivative represented by Structural Formula (I). Typically, this reaction is carried out in the presence of a base.

The above described methods may additionally comprise the step of purifying or ultrapurifying the synthesis products by resolving enantiomers or diastereomers of the products. The cysteine derivative formed can be the (R) or (S)-isomer or a mixture thereof. Additionally, the methods can comprise the isolation of the enantiomers of the synthesis products. In a preferred embodiment, the methods of the present invention comprise isolating the (S)-enantiomer of 2-alkylcysteine.

The present invention also relates to a method of preparing a substituted thiazoline carboxylic acid represented by Structural Formula (VII):

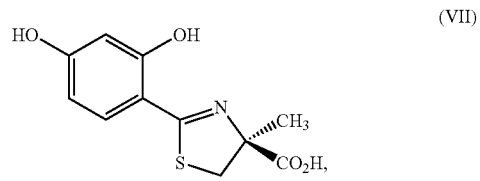

or a salt thereof.

In one embodiment, the method comprises:
(a) reacting, in the presence of a phase transfer catalyst, an (R)-cysteine derivative represented by Structural Formula (VIII):

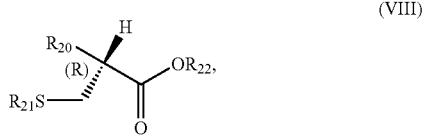

or a salt thereof, wherein
$R_{20}$ is —$NH_2$; —$N(R_{25})(R_{26})$; —$NHR_{26}$; or —$N=R_{27}$, wherein $R_{24}$, $R_{25}$, $R_{26}$, and $R_{27}$ are, independently, a substituted or unsubstituted alkyl group, a substituted or unsubstituted aromatic group, or a substituted or unsubstituted heterocyclic group; and
$R_{21}$ and $R_{22}$ are, independently, —H, a substituted or unsubstituted alkyl group, a substituted or unsubstituted aromatic group, or a substituted or unsubstituted heterocyclic group; with a compound having the formula $CH_3$-L, wherein L is a leaving group, thereby forming a 2-methylcysteine derivative represented by Structural Formula (IX):

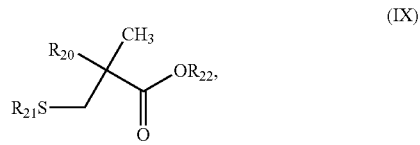

or a salt thereof;
(b) optionally, purifying the (S)-isomer of the 2-methylcysteine derivative;
(c) reacting the (S)-isomer of the 2-methylcysteine derivative with acid to form a (S)-2-methylcysteine represented by Structural Formula (X):

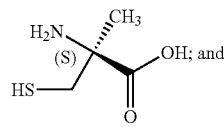

(d) coupling the (S)-2-methylcysteine with 2,4-dihydroxybenzonitrile thereby forming the substituted thiazoline carboxylic acid represented by Structural Formula (VII).

A further embodiment of the invention includes reacting a cysteine or derivative thereof, including ester and amide derivatives, with a benzonitrile to form a 2-phenyl thiazoline. Suitable cysteines are preferably substantially enantiomerically pure. Suitable cysteines can also be substituted at the 2- and 3-positions, preferably alkylated. Preferred cysteines include, separately, the (R)- and (S)-enantiomers of 2-methylcysteine, 3,3-dimethylcysteine and 2,3,3-trimethylcysteine, along with esters (e.g., methyl, ethyl) thereof. Benzonitrile are preferably substituted, such as 2,4-dihydroxybenzonitrile, 2-hydroxybenzonitrile, 2,4-dibenyzloxybenzonitrile and 2-benzyloxybenzonitrile. The reaction involves reacting the cysteine and the benzonitrile with a trialkylamine (e.g., trimethylamine, triethylamine, tripropylamine) in an alcoholic solvent (e.g., methanol, ethanol, n-propanol, isopropanol). Preferably, the trialkylamine is triethylamine and the solvent is ethanol. The reaction mixture is advantageously heated to a temperature from about 50 degrees C. to about 150 degrees C., where the mixture refluxes. Also, the reaction is preferably conducted under an inert atmosphere (e.g., nitrogen, argon, mixtures thereof).

Advantages of the present invention include the facile synthesis of a 2-alkylcysteine from cysteine, an inexpensive and readily available starting material. 2-Methylcysteine prepared by the method of the present invention can be coupled to 2,4-dihydroxybenzonitrile to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

The present invention provides useful and efficient methods of preparing 2-alkylcysteine derivatives. The methods include forming a 2-alkylcysteine derivative from a cysteine derivative in the presence of a phase transfer catalyst. Additionally, the present invention relates to the preparation of 4,5-dihydro-2-(2,4-dihydroxyphenyl)-4-alkyl-thiazole-4-carboxylic acid. In particular, the present invention provides methods for preparing 2-methylcysteine derivatives as well as 4,5-dihydro-2-(2,4-dihydroxyphenyl)-4-methylthiazole-4-carboxylic acid.

In one aspect, the present invention relates to a method of preparing a 2-alkylcysteine derivative represented by Structural Formula (I):

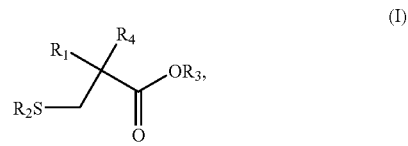

or a salt thereof, wherein
$R_1$ is —$NH_2$; —$N(R_5)(R_6)$; —$NHR_7$; or —$N=R_8$; wherein $R_5$, $R_6$, $R_7$, and $R_8$ are, independently, a substituted or unsubstituted alkyl group, a substituted or unsubstituted aromatic group, or a substituted or unsubstituted heterocyclic group;
$R_2$ and $R_3$ are, independently, —H, a substituted or unsubstituted alkyl group, a substituted or unsubstituted aromatic group, or a substituted or unsubstituted heterocyclic group; and
$R_4$ is a substituted or unsubstituted alkyl group.

In one embodiment, the method comprises reacting a cysteine derivative represented by Structural Formula (II):

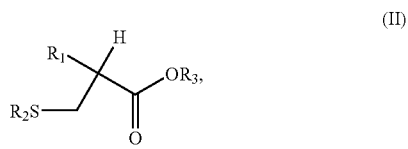

or a salt thereof, wherein $R_1$, $R_2$ and $R_3$ are defined as above, with a compound having the formula $R_4$-L, wherein $R_4$ is defined as above and L is a leaving group, in the presence of a phase transfer catalyst thereby forming the 2-alkylcysteine derivative represented by Structural Formula (I).

In a preferred embodiment, the cysteine derivative reacted is the (R) isomer, represented by Structural Formula (IV):

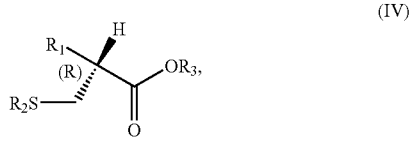

(IV)

or a salt thereof, wherein $R_1$, $R_2$, and $R_3$ are as defined above. In an especially preferred embodiment, the cysteine derivative reacted is a protected (R)-cysteine and the 2-alkylcysteine derivative thereby formed is a protected 2-methylcysteine. Either the (R) or the (S)-enantiomer of the 2-alkylcysteine derivative may be formed in enantiomeric excess. Preferably, the (S)-isomer of a 2-alkylcysteine derivative is formed in enantiomeric excess. More preferably, the (S)-isomer of a protected 2-methylcysteine is formed in enantiomeric excess.

The resulting enantiomers of the product can be further resolved and isolated into pure or substantially pure enantiomer components.

Functional groups in compounds of the present invention can be protected with protecting groups. Preferably, the cysteine derivative is protected at any reactive site, for example, at the amino, —SH, and/or carboxyl sites of cysteine. A protecting group reduces or eliminates the ability of a functional group to react under certain conditions. For example, a thiol or an alcohol can be protected with an acyl group. Similarly, an alcohol or a thiol can be protected by a trityl, a benzyloxymethyl, a tetrahydropyranyl or a trimethylsilyl group. An amine can, for example, be protected by an Fmoc group or a Boc group. An acid group can be protected, for example, by forming an ester or a carboxamide group. Additional protecting groups, methods of adding a protecting group, and methods of removing a protecting group are taught in "Protective Groups in Organic Synthesis, 3$^{rd}$ Edition" by Peter G. M. Wuts and Theodora W. Greene, Wiley-Interscience, 1999, the entire contents of which are incorporated herein by reference.

Preferred protecting groups for acidic nitrogen atoms include formyl; 4-toluenesulfonyl; t-butyloxycarbonyl; 2,4-dinitrophenyl; benzyloxymethyl; t-butoxymethyl; 2-chlorobenzyloxy-carbonyl; allyloxycarbonyl; benzyloxycarbonyl (Z); mesitylene-2-sulfonyl; 4-methyloxy-2,3,6-trimethyl-benzyenesulfonyl; 2,2,5,7,8-pentamethyl-chroman-6-sulfonyl; 9-xanthenyl; and 2,4,6-trimethoxybenzyl.

In one embodiment, $R_1$ is a protected amino group such as —N=C(Ar)$_2$ wherein each Ar is, independently, a substituted or unsubstituted aryl group. For example, $R_1$ can be a benzophenone imine represented by Structural Formula (III):

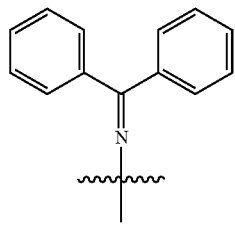

(III)

Preferred protecting groups for acidic sulfur groups include 4-methylbenzyl; 3-nitro-2-pyridinesulfenyl; trityl; 2,4,6-trimethoxybenzyl; acetamidomethyl; trimethylacetaminomethyl; t-butylsulfonyl; and sulfoxide.

In one embodiment, $R_2$ is a protecting group protecting the cysteine —SH group. For example $R_2$ can be —C(Ar)$_3$ wherein each Ar is, independently, a substituted or unsubstituted aryl group. Preferably, $R_2$ is trityl.

Preferred protecting groups for acidic oxide groups include benzyl ether; t-butyl ether; benzyl ether; 2,6-dichlorobenzyl ether; 2-bromobenzyl ether; and 3,5-dibromobenzyl ether.

Carboxyl groups can be protected, for example, as esters or as carboxamides. For example, when a carboxyl group is protected as an ester, it takes the form of —COOR wherein R is a substituted or unsubstituted C1 to C10 alkyl group, a substituted or unsubstituted up to C30 aryl group, or a substituted or unsubstituted alkyl-aryl group wherein the alkyl group is C1 to C5 and the aryl group is up to C30. When a carboxyl group is protected as a carboxamide, it takes the form of —CONR'R" wherein R' and R" are, independently, —H, a substituted or unsubstituted C1 to C10 alkyl group, a substituted or unsubstituted up to C30 aryl group, or a substituted or unsubstituted alkyl-aryl group wherein the alkyl group is C1 to C5 and the aryl group is up to C30.

For example, $R_3$ can be a carboxyl protecting group such as a substituted or unsubstituted C1 to C10 alkyl group. In a preferred embodiment, $R_3$ is t-butyl.

In one incarnation of the present invention, as illustrated below, the cysteine derivative is 2(R)-(benzhydrylideneamino)-3-tritylsulfanyl-propionic acid tert-butyl ester. 2(R)-(Benzhydrylidene-amino)-3-tritylsulfanyl-propionic acid tert-butyl ester can be formed by the following process: (1) 2(R)-(9H-Fluoren-9-ylmethoxycarbonylamino)-3-tritylsulfanyl-propionic acid (i.e., (R)-cysteine with Fmoc a protected amino group and with a trityl protected —SH group), is reacted with t-butyl alcohol and dicyclohexyl carbodiimide (DCC) in 4-(dimethylamino)pyridine (DMAP) and tetrahydrofuran (THF) at room temperature to form 2(R)-(9H-fluoren-9-ylmethoxycarbonylamino)-3-tritylsulfanyl-propionic acid tert-butyl ester; (2) the Fmoc group is removed from the 2(R)-(9H-fluoren-9-ylmethoxycarbonylamino)-3-tritylsulfanyl-propionic acid tert-butyl ester using either diethylamine in dichloromethane or piperidine in dichloromethane to form 2(R)-amino-3-tritylsulfanyl-propionic acid tert-butyl ester; and (3) the 2(R)-amino-3-tritylsulfanyl-propionic acid tert-butyl ester is reacted with benzhydrylideneamine in dichloromethane at room temperature to form 2(R)-(benzhydrylidene-amino)-3-tritylsulfanyl-propionic acid tert-butyl ester.

The following sequence illustrates the method described above of forming 2(R)-(benzhydrylidene-amino)-3-tritylsulfanyl-propionic acid tert-butyl ester from 2(R)-(9H-Fluoren-9-ylmethoxycarbonylamino)-3-tritylsulfanyl-propionic acid:

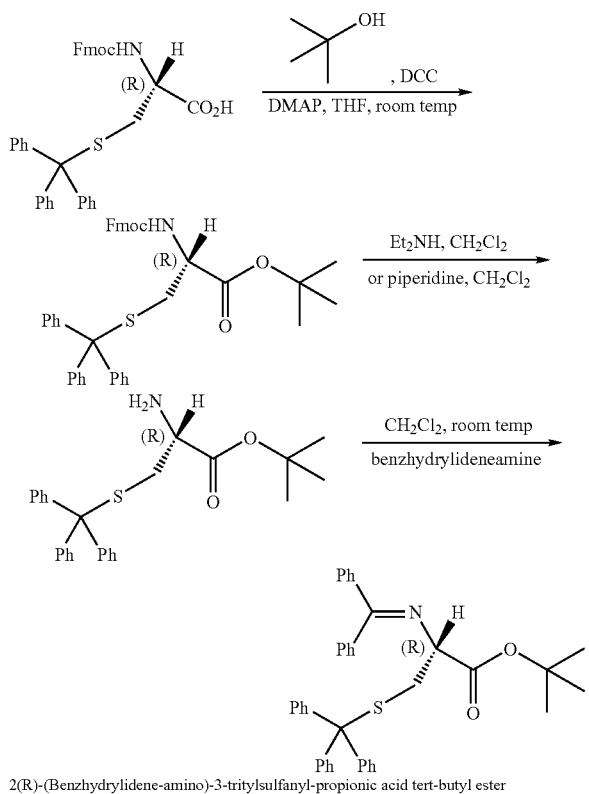

2(R)-(Benzhydrylidene-amino)-3-tritylsulfanyl-propionic acid tert-butyl ester

In one embodiment, the cysteine derivative represented by Structural Formula (II) can be alkylated in the presence of one or more bases, an alkylating agent, and a phase transfer catalyst. For example, 2-(benzhydrylidene-amino)-3-tritylsulfanyl-propionic acid tert-butyl ester is reacted with cesium hydroxide monohydrate and excess methyl iodide in dichloromethane at about −80° to −60° C. and in the presence of a phase transfer catalyst. Preferably, the cysteine derivative is alkylated using a phase transfer catalyst such that an enantiomeric excess of either the (R) or (S)-isomer is produced (i.e., the alkylation is stereo selective).

Alkylating agents can have the formula $R_4$-L, where $R_4$ is a substituted or unsubstituted alkyl group and L is a leaving group. Preferred $R_4$ groups include substituted or unsubstituted C1–C4 alkyl groups; methyl and benzyl are especially preferred $R_4$ groups. The leaving group L is typically a weak base. Suitable leaving groups include halogen, tosyl, mesyl, triflyl, brosyl, p-nitrophenyl, and 2,4-dinitrophenyl groups. Halogens include bromine, chlorine, and iodine. Iodine is a preferred leaving group. Suitable amounts of alkylating agent can include about 1 to 20, about 2 to 15, about 3 to 10, or, preferably, about 5 equivalents, relative to the amount of cysteine derivative.

Preferred bases include alkali or alkaline earth metal hydroxides, alkoxides, amides, or carbonates or their combinations. Available bases include potassium t-butoxide, sodium methoxide, sodium ethoxide, sodium amide, calcium carbonate, cesium carbonate, and the alkali metal salts of hexamethyl disilazide (HMDS). Preferred bases include potassium hydroxide, sodium hydroxide, and cesium hydroxide monohydate. Suitable amounts of base include about 5 to 25, about 10 to 20, about 10 to 15, or, preferably, about 10 equivalents, relative to the amount of cysteine derivative.

A phase transfer catalyst functions at the boundary between two solvents or mixtures of solvents, at least one of which is an organic solvent. The organic phase of the process can include any organic solvent which is substantially inert to the catalyst, reactants and products. The organic phase may comprise a combination of two or more solvents. Solvents generally include, but are not limited to, aprotic solvents such as acetonitrile, acetone, dimethylformamide, dimethyl sulfoxide, tetrahydrofuran, and hexamethylphosphoramide. In a preferred embodiment, the organic phase is comprises dichloromethane.

The alkylation of the cysteine derivative can be performed at temperatures ranging from about −80° C. to about room temperature such as between about −80° and 0° C. In a preferred embodiment, the alkylation is performed at temperatures of between about −80° and −40° C., for example, at about −60° C.

In one aspect of the present invention, a cinchona-alkaloid derived phase transfer catalyst is used to alkylate a cysteine derivative. In one particular embodiment, a cinchona-alkaloid derived phase transfer catalyst is used to stereoselectively alkylate a 2-(benzhydrylidene-amino)-3-tritylsulfanyl-propionic acid tert-butyl ester at the 2-carbon position. The phase transfer catalyst can be derived from cinchonine or from cinchonidine. Use of one of these catalysts in the alkylation reaction can yield enantiomeric excesses of either the (R) or (S)-enantiomer of the alkylated cysteine derivative, while use of an enantiomer of that catalyst can yield enantiomeric excesses of the other enantiomer of the alkylated cysteine derivative. Thus by selecting the phase transfer catalyst used, one can direct which enantiomer of the alkylated cysteine derivative will form.

In a preferred embodiment, the phase transfer catalyst used is derived from cinchonidine and is represented by Structural Formula (V):

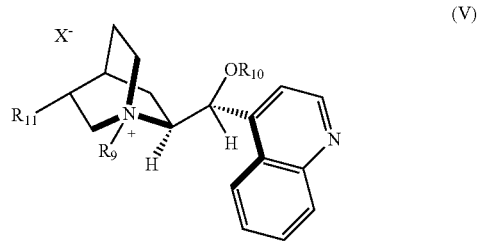

(V)

wherein
$R_9$ is a substituted or unsubstituted alkyl group, a substituted or unsubstituted aromatic group, or a substituted or unsubstituted heterocyclic group;
$R_{10}$ and $R_{11}$ are, independently, —H, a substituted or unsubstituted alkyl group, a substituted or unsubstituted aromatic group, or a substituted or unsubstituted heterocyclic group; and
X is a halogen.

$R_9$ can be, for example, substituted or unsubstituted napthyl, anthracenylmethyl, or benzyl. Preferably, $R_9$ is 9-anthracenylmethyl as represented by Structural Formula (VI):

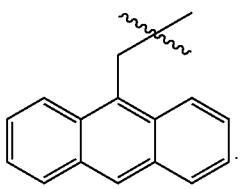

(VI)

$R_{10}$ can be, for example, substituted or unsubstituted allyl or benzyl. Preferably, $R_{10}$ is substituted or unsubstituted allyl. In another preferred embodiment, $R_{11}$ is substituted or unsubstituted ethenyl. In another, X is chlorine or bromine. Thus the phase transfer catalyst can be represented by Structural Formula (XI):

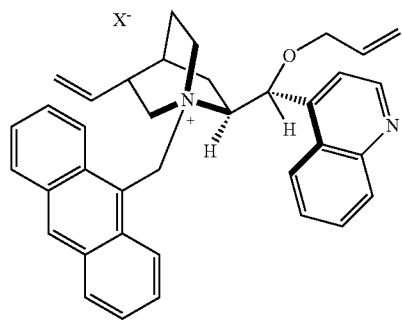

(XI)

Additional examples of phase transfer catalysts suitable for use in the present invention are described in U.S. Pat. No. 5,554,753 issued to O'Donnell, et al., the entire teachings of which are incorporated herein by reference.

The phase transfer catalyst represented by Structural Formula (XI) is preferably prepared using the following method as described by Corey, et al., in "A Rational Approach to Catalytic Enantioselective Enolate Alkylation Using a Structurally Rigidified and Defined Chiral Quaternary Ammonium Salt Under Phase Transfer Conditions" (J. Am. Chem. Soc. 119, 12414–12415 and Corey Supplemental therein 1–25 (1997)), the entire contents of which are incorporated by reference herein by reference. In that method, cinchonidine, represented by Structural Formula (XII):

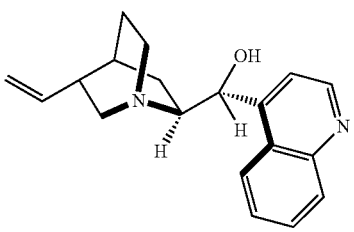

(XII)

is suspended in toluene and 9-(chloromethyl)anthracene, represented by Structural Formula (XIII):

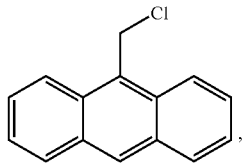

(XIII)

is added. The mixture is stirred at reflux for about 2 hours. The product, N-9-anthracenylmethylcinchonidinium chloride represented by Structural Formula (XIV):

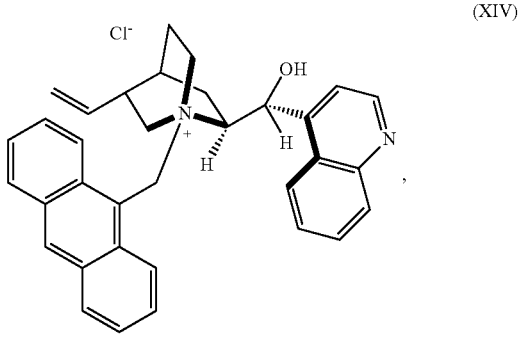

(XIV)

is collected as a light yellow solid. The N-9-anthracenylmethylcinchonidinium chloride is then suspended in dichloromethane. To this suspension is added 50% KOH and allyl bromide. The resulting mixture is then stirred for about 4 hours at about 23° C. The product, O(9)-allyl-N-9-anthracenylmethylcinchonidium bromide represented by Structural Formula (XI), is collected as a light orange solid.

The use of O(9)-allyl-N-9-anthracenylmethylcinchonidium bromide as a phase transfer catalyst is also described in co-pending U.S. patent application Ser. Nos. 60/380,903, filed May 15, 2002 and 60/392,833, filed Jun. 27, 2002, the entire contents of which are incorporated herein by reference.

Examples of other phase transfer catalysts include benzyl triethyl ammonium chloride, benzyl trimethyl ammonium chloride, benzyl tributyl ammonium chloride, tetrabutyl ammonium bromide, tetraethyl ammonium bromide, tetrabutyl ammonium hydrogen sulfate, tetramethyl ammonium iodide, tetramethyl ammonium chloride, triethylbutyl ammonium bromide, tributyl ethyl ammonium bromide, tributyl methyl ammonium chloride, 2-chloroethylamine chloride HCl, bis(2-chloroethyl)amine HCl, 2-dimethylaminoethyl chloride HCl, 2-ethylaminoethyl chloride HCl, 3-dimethylaminopropyl chloride HCl, methylamine HCl, dimethylamine HCl, trimethylamine HCl, monoethylamine HCl, diethylamine HCl, triethylamine HCl, ethanolamine HCl, diethanolamine HCl, triethanolamine HCl, cyclohexylamine HCl, dicyclohexylamine HCl, cyclohexylamine HCl, diisopropylethylamine HCl, ethylenediamine HCl, aniline HCl, methyl salicylate, ethyl salicylate, butyl salicylate amyl salicylate, isoamyl salicylate, 2-ethylsalicylate, and benzyl salicylate.

In one form of the present invention, the phase transfer catalyst, such as O(9)-allyl-N-9-anthracenylmethylcinchonidium bromide, is present in an amount of about 0.05 to 0.4 equivalents relative to the amount of cysteine derivative.

Alternatively, the phase transfer catalyst can be present between about 0.05 and 0.25 equivalents, between about 0.1 and 0.15 equivalents, or, preferably, at about 0.1 equivalents (relative to the amount of cysteine derivative).

In a preferred embodiment, (R)-2-(benzhydrylidene-amino)-3-tritylsulfanyl-propionic acid tert-butyl ester is reacted with cesium hydroxide monohydrate and excess methyl iodide in dichloromethane at about −60° C. and in the presence of O(9)-allyl-N-9-anthracenylmethylcinchonidium bromide thereby forming (S)-2-(benzhydrylidene-amino)-2-methyl-3-tritylsulfanyl-propionic acid tert-butyl ester.

Protecting groups, if present, can be removed from the 2-alkylcysteine derivative. Methods of removing a protecting group are well known in the art and taught in "Protective Groups in Organic Synthesis, $3^{rd}$ Edition" by Wuts and Greene, incorporated by reference above. For example, 2(S)-(benzhydrylidene-amino)-2-methyl-3-tritylsulfanyl-propionic acid tert-butyl ester can be reacted with acid thereby forming (S)-2-methylcysteine.

The products, either enantiomers or diastereomers, of the above noted syntheses can be purified or ultrapurified before or after any protecting groups are removed. In a preferred embodiment, the 2-alkylcysteine derivative (e.g., 2-methylcysteine) is purified by resolution into the (R) and (S)-isomers based on the cysteine 2-carbon position. For example, the 2-alkylcysteine derivative can be purified or ultrapurified using the technique of emulsion crystallization. Emulsion crystallization may be used to purify acids and functionalized derivative of acids such as esters and amides. Optionally, the protective groups are removed after purification to form an unprotected (S)-, or (R)-, 2-alkylcysteine (e.g., 2-methylcysteine) or an (S)-, or (R)-, 2-alkylcysteine derivative.

Alternatively, protective groups are removed from the 2-alkylcysteine derivative to form an unprotected 2-alkylcysteine prior to further resolution. For example, protective groups are removed from a protected 2-methylcysteine to form an unprotected 2-methylcysteine, the unprotected 2-methylcysteine is resolved into its (R) and (S)-isomers, and an (S)-2-alkylcysteine is isolated. The 2-alkylcysteine can be resolved into its (R) and (S)-isomers using the technique of emulsion crystallization, or the 2-alkylcysteine can be resolved into its enantiomers by forming a diastereomeric salt.

Chiral carboxylic acids and their functionalized derivatives, such as 2-alkylcysteines and their derivatives, can be purified by emulsion crystallization, as described in U.S. Pat. Nos. 5,872,259, 6,383,233 and 6,428,583, issued to Reuter, the entire teachings of which are incorporated herein by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication eventually helps the process of forming an emulsion. The mixture is then seeded with crystals of the desired, optically active acid along with an additional quantity of surfactant and an anti-foaming agent. The desired product usually crystallizes out and can be separated by filtration.

Chiral carboxylic acids also can be purified through further resolution by forming a diastereomeric salt with the chiral carboxylic acid and a chiral amine. Suitable chiral amines include arylalkylamines such as 1-alkyl-1-aminoalkanes and 1-aryl-1-aminoalkanes. Examples include (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Preferably, (R)-1-phenylethylamine is used to further resolve the chiral carboxylic acid mixture. Resolution of chiral compounds using diastereomeric salts is further described in *CRC Handbook of Optical Resolutions via Diastereomeric Salt Formation* by David Kozma (CRC Press, 2001), incorporated herein by reference in its entirety.

Once the chiral carboxylic acids or their derivatives have been purified, the desired isomer can be isolated. Typically, the (S)-isomer is isolated. For example, protected or unprotected (S)-2-methylcysteine, (S)-2-alkylcysteines, or (S)-2-alkylcysteine derivatives are isolated. Preferably, a protected (S)-2-methylcysteine is isolated.

In a preferred embodiment, a protected (S)-2-methylcysteine is formed and isolated. (S)-2-methylcysteine can then be formed by removing any protecting groups present, for example, by treating the protected (S)-2-methylcysteine with acid to remove protecting groups. Cysteine or a 2-alkylcysteine such as (S)-2-methylcysteine can be coupled to a substituted or unsubstituted aryl nitrile such as a substituted or unsubstituted benzonitrile. Preferably, the substituents on benzonitrile will not interfere with the coupling reaction. In another preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin). In yet another embodiment, (S)-2-methylcysteine is coupled to 2-hydroxybenzonitrile to form 4,5-dihydro-2-(2-hydroxyphenyl)-4-methylthiazole-4(S)-carboxylic acid (also known as desazadesferrithiocin).

Typically, coupling of cysteine or a 2-alkylcysteine and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. The benzimidate is then reacted with the cysteine (or related compound) under basic conditions. Acceptable bases include trimethylamine, triethylamine, triphenylamine, and the like. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

Suitable benzonitriles and benzimidates for use in the above coupling reaction can be synthesized by methods described in co-pending U.S. Patent Application No. 60/381, 013, entitled "Synthesis of Benzonitriles from Substituted Benzoic Acid," filed May 15, 2002, co-pending U.S. Patent Application No. 60/380,878, entitled "Synthesis of Benzonitriles from Substituted Benzaldehyde," filed May 15, 2002, and co-pending U.S. Patent Application No. 60/380,909, entitled "Synthesis of Benzimidate from Benzoic Acid," filed May 15, 2002. The entire contents of these applications are incorporated herein by reference.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080, all issued to Bergeron, the contents of which are incorporated herein by reference. Additional examples can be found in International Application Nos. PCT/US93/10936, published as WO 94/1137 on May 5, 1994; PCT/US97/04666, published as WO 97/36885 on Oct. 9, 1997; and PCT/US99/19691, published as WO 00/12493 on Mar. 9, 2000, the entire contents of which are incorporated herein by reference.

An alkyl group is a hydrocarbon in a molecule that is bonded to one other group in the molecule through a single covalent bond from one of its carbon atoms. Alkyl groups can be cyclic, branched or unbranched, and/or saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazoly, 4-oxazolyl and 5-oxazolyl.

Aromatic groups also include fused polycyclic aromatic ring systems in which a carbocyclic, alicyclic, aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl and aryl groups include —OH, halogen (—Br, —Cl, —I and —F), —O(R'), —O—CO—(R'), —CN, —NO₂, —COOH, =O, —NH₂, —NH(R'), —N(R')₂, —COO(R'), —CONH₂, —CONH(R'), —CON(R')₂, —SH, —S(R'), guanidine, alkyl, and aryl. Each R' is, independently, an alkyl group or an aromatic group. A substituted alkyl or aryl group can have more than one substituent.

Also included in the present invention are salts of the disclosed carboxylic acids. For example, amino acids can also be present in the anionic, or conjugate base, form, in combination with a cation. Suitable cations include alkali metal ions, such as sodium and potassium ions; alkaline earth ions, such as calcium and magnesium ions; and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

EXEMPLIFICATION

Example 1

Preparation of the Phase Transfer Catalyst

A cinchonidine derived phase transfer catalyst is prepared as follows. About 4 grams of cinchonidine is suspended in about 40 mL of toluene. About 3 grams of 9-(choloromethyl) anthracene is then added to the suspension. The mixture is heated to reflux and stirred for about 2 hours. Solids are cooled to room temperature, poured onto about 200 mL of diethyl ether and filtered. The product collected is N-9-anthracenylmethylcinchonidinium chloride.

About 5 grams N-9-anthracenylmethylcinchonidinium chloride is then suspended in about 40 mL dichloromethane. Then about 2.5 mL allyl bromide and about 5 mL of 50% KOH (aq) are added to the suspension. The mixture is stirred at about room temperature for about 4 hours. Fifty milliliters of water is then added to the mixture and the mixture is extracted using three aliquots of dichloromethane. The organic extracts are combined and dried over $Na_2SO_4$, filtered, and concentrated in vacuo. Recrystalization of the residue from methanol-diethyl ether at −20° C. yields the product, O(9)-allyl-N-9-anthracenylmethylcinchonidium bromide.

Example 2

Preparation of (S)-2-Methylcysteine

2(R)-(9H-Fluoren-9-ylmethoxycarbonylamino)-3-tritylsulfanyl-propionic acid is reacted with t-butyl alcohol and dicyclohexyl carbodiimide (DCC) in 4-(dimethylamino) pyridine (DMAP) and tetrahydrofuran (THF) at room temperature to form 2(R)-(9H-fluoren-9-ylmethoxycarbonylamino)-3-tritylsulfanyl-propionic acid tert-butyl ester.

The Fmoc group is removed from the 2(R)-(9H-fluoren-9-ylmethoxycarbonylamino)-3-tritylsulfanyl-propionic acid tert-butyl ester using diethylamine in dichloromethane to form 2(R)-amino-3-tritylsulfanyl-propionic acid tert-butyl ester The 2(R)-amino-3-tritylsulfanyl-propionic acid tert-butyl ester is reacted with benzhydrylideneamine in dichloromethane at room temperature to form 2(R)-(benzhydrylidene-amino)-3-tritylsulfanyl-propionic acid tert-butyl ester.

A mixture of 2(R)-(benzhydrylidene-amino)-3-tritylsulfanyl-propionic acid tert-butyl ester (one equivalent), about 10 equivalents cesium hydroxide monohydrate, about 0.1 equivalents of O(9)-allyl-N-9-anthracenylmethylcinchonidium bromide, and about 0.5 mL dichloromethane is prepared. Excess methyl iodide (about 5 equivalents) is then added dropwise at about −80° C. to the above formed mixture. The mixture is then stirred and allowed to react for about 25–30 hours at about −60° C. The reacted mixture is then diluted with ether, washed with water, washed with brine, dried over $MgSO_4$, filtered and concentrated in vacuo. The product collected is 2-(benzhydrylidene-amino)-2-methyl-3-tritylsulfanyl-propionic acid tert-butyl ester with the (S)-isomer in enantiomeric excess.

The 2-(benzhydrylidene-amino)-2-methyl-3-tritylsulfanyl-propionic acid tert-butyl ester is resolved using emulsion crystallization. 2(S)-(benzhydrylidene-amino)-2-methyl-3-tritylsulfanyl-propionic acid tert-butyl ester is then isolated and reacted with excess 5M hydrochloric acid to form (S)-2-methylcysteine.

Example 3

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20° C.)

45 mg of (R,R)- and (S,S)-amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)-(−) amino acid or its ester crystals grown under similar conditions. After 2 hours of agitation the resulting crystals were filtered off, washed with water and dried in a gentle nitrogen stream.

Example 4

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S enantiomer.

Example 5

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4(S)-carboxylic acid product. $^1$H-NMR showed no significant impurity.

Example 6

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

We claim:

1. A method of preparing a 2-alkylcysteine derivative represented by Structural Formula (I):

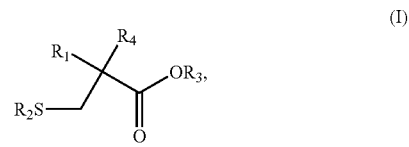

or a salt thereof, wherein $R_1$ is —$NH_2$; —$N(R_5)(R_6)$; —$NHR_7$; or —$N=R_8$; wherein $R_5$, $R_6$, $R_7$, and $R_8$ are, independently, a substituted or unsubstituted alkyl group, a substituted or unsubstituted aromatic group, or a substituted or unsubstituted heterocyclic group;

$R_2$ and $R_3$ are, independently, —H, a substituted or unsubstituted alkyl group, a substituted or unsubstituted aromatic group, or a substituted or unsubstituted heterocyclic group; and $R_4$ is a substituted or unsubstituted alkyl group;

the method comprising, reacting, in the presence of a phase transfer catalyst, a cysteine derivative represented by Structural Formula (II):

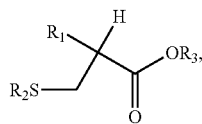

or a salt thereof, wherein $R_1$, $R_2$ and $R_3$ are defined as above;

with a compound having the formula $R_4$-L, wherein $R_4$ is defined as above and L is a leaving group thereby forming the 2-alkylcysteine derivative represented by Structural Formula (I), wherein the phase transfer catalyst is a compound represented by Structural Formula (V):

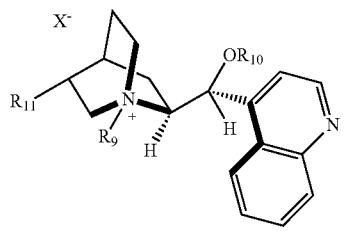

wherein $R_9$ is a substituted or unsubstituted alkyl group, a substituted or unsubstituted aromatic group, or a substituted or unsubstituted heterocyclic group;

$R_{10}$ and $R_{11}$ are, independently, —H, a substituted or unsubstituted alkyl group, a substituted or unsubstituted aromatic group, or a substituted or unsubstituted heterocyclic group; and X is a halogen.

2. The method of claim 1 wherein $R_1$ is —N=C(Ar)$_2$ wherein each Ar is, independently, a substituted or unsubstituted aryl group.

3. The method of claim 2 wherein $R_1$ is a benzophenone imine represented by Structural Formula (III):

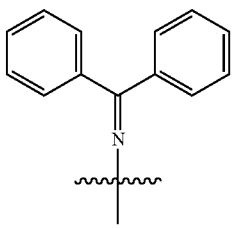

4. The method of claim 1 wherein $R_2$ is —C(Ar)$_3$ wherein each Ar is, independently, a substituted or unsubstituted aryl group.

5. The method of claim 4 wherein $R_2$ is trityl.

6. The method of claim 1 wherein $R_3$ is a substituted or unsubstituted C1 to C10 alkyl group.

7. The method of claim 6 wherein $R_3$ is t-butyl.

8. The method of claim 1 wherein the cysteine derivative is the (R) isomer, represented by Structural Formula (IV):

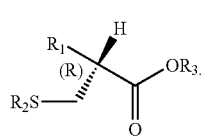

9. The method of claim 1 wherein $R_4$ is a substituted or unsubstituted C1 to C4 alkyl group.

10. The method of claim 8 wherein $R_4$ is methyl.

11. The method of claim 1 wherein L is iodine.

12. The method of claim 1 wherein the cysteine derivative is protected at any acidic nitrogen, oxygen, or sulfur atoms.

13. The method of claim 1 wherein $R_9$ is 9-anthracenylmethyl, represented by the Structural Formula (VI):

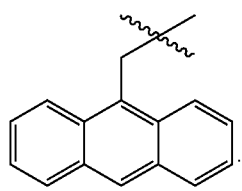

14. The method of claim 1 wherein R10 is substituted or unsubstituted allyl.

15. The method of claim 1 wherein R11 is substituted or unsubstituted ethenyl.

16. The method of claim 1 wherein X is chlorine.

17. The method of claim 1 further comprising the step of resolving the enantiomers of the 2-alkylcysteine derivative.

18. The method of claim 17 wherein the (S)-isomer of the 2-alkylcysteine derivative is isolated.

* * * * *